United States Patent [19]

Hasebe et al.

[11] Patent Number: 4,971,062
[45] Date of Patent: Nov. 20, 1990

[54] FINGERTIP PULSE WAVE SENSOR

[75] Inventors: Noboru Hasebe; Shoji Ito, both of Tokyo, Japan

[73] Assignee: Misawa Homes Institute of Research and Development, Tokyo, Japan

[21] Appl. No.: 329,579

[22] Filed: Mar. 28, 1989

[30] Foreign Application Priority Data

Sep. 24, 1988 [JP] Japan .................................. 63-237535

[51] Int. Cl.$^5$ .................................................. A61B 6/00
[52] U.S. Cl. ...................................... 128/664; 128/666; 128/687
[58] Field of Search ................................ 128/664–677, 128/632–633, 672, 677, 686, 687–690

[56] References Cited

U.S. PATENT DOCUMENTS

| | | | |
|---|---|---|---|
| 3,810,460 | 5/1974 | Van Nie | 128/666 |
| 4,116,228 | 9/1978 | Hudspeth et al. | 128/689 X |
| 4,334,544 | 6/1982 | Hill et al. | 128/664 |
| 4,685,464 | 8/1987 | Goldberger et al. | 128/664 X |

FOREIGN PATENT DOCUMENTS 2524792 10/1983 France ................................ 128/664

*Primary Examiner*—Max Hindenburg
*Assistant Examiner*—J. P. Lacyk
*Attorney, Agent, or Firm*—Hoffmann & Baron

[57] ABSTRACT

A fingertip pulse wave sensor includes a fingertip cushion supporting member having a fingertip cushion supporting surface, and a nail supporting member having a nail supporting surface which is disposed in opposed relationship with the fingertip cushion supporting surface at an interval smaller than the standard thickness of fingertips. Either of the fingertip cushion supporting member of the nail supporting member is fixed, and the other of the fingertip cushion supporting member and the nail supporting member is hinged. The hinged fingertip cushion supporting member or nail supporting member is urged in the direction in which they are moved to each other by an elastic body which is capable of applying a substantially fixed amount of pressure with respect to the variations in the pivot stroke caused by the variations in the thickness of the fingertips resting on the fingertip cushion supporting member. The fingertip pulse wave sensor also includes a light-emitting element which is disposed on either of the fingertip cushion supporting surface and the nail supporting surface, and a light-receiving element which is disposed on the other of the fingertip cushion supporting surface and the nail supporting surface.

2 Claims, 1 Drawing Sheet

FINGERTIP PULSE WAVE SENSOR

BACKGROUND OF THE INVENTION

1. Field of the Invention:

The present invention relates to a fingertip pulse wave sensor for detecting changes in the volume of a blood vessel in a fingertip held between a light-emitting element and a light-receiving element, in which the changes are caused by pulsation and detected as electrical signals produced in response to changes in the intensity of the light transmitted through the fingertip.

2. Description of the Related Art:

A conventional fingertip pulse wave sensor of the above-described type includes a pad with either a light-receiving element or a light-emitting element buried therein which makes contact with a fingernail, and a pad which has the other of the light-receiving and light-emitting elements buried therein and which makes contact with a fingertip cushion. These pads are disposed in opposed relationship with each other. The conventional fingertip pulse wave detector also includes a plate spring having a U-shaped form and is mounted on the rear surface of either of the pads so as to hold the fingertip between the two pads and under pressure.

With this arrangement, although the fingertip can be elastically held in place in spite of the variations naturally occurring in the shape of the fingertips of different individuals or any irregularities in the top dead point of the plate spring employed, these variations or irregularities serve to cause variations in the amount of pressure applied to the finger to a considerable extent. For example, in the case of a spring designed to provide a force that will press a fingertip with a deflection of 3 mm, if a deflection of 6 mm is caused due to differences in the shape of different individuals' fingertips or irregularities in the top dead point of the spring employed, it is possible that the pressure applied to the fingertip will be completely different. Excessive pressure exerted on a portion to be measured, increases the amount of blood in the venula of the fingertip, which is being returned to the associated vein. This has an effect on the waveform of a pulse, which is produced during arterial pulse wave detection at the fingertip.

This is undesirable in terms of the measurement precision in a plethysmograph which is designed to estimate the form of a waveform in its detected state. This greatly affects the results of measurements obtained using an "acceleration type" fingertip pulse wave detector which must be able to non-invasively monitor the state of a peripheral circle by converting the waveform detected to an acceleration curve. This conversion is achieved by differentiating twice the detected waveform with respect to the time. This conversion requirement, in effect, prevents such an "acceleration-type" fingertip pulse wave detector from being employable in clinical applications.

SUMMARY OF THE INVENTION

Accordingly, an object of the present invention is to provide a fingertip pulse wave sensor which is capable of detecting a fingertip pulse wave in a consistent manner and with a high degree of accuracy in spite of differences naturally occurring in the shape of fingertips among different individuals.

In order to achieve this object, the present invention provides a fingertip pulse wave sensor which is based on the confirmation that application of a certain amount of pressure is inevitable for stable pulse wave detection.

The fingertip pulse have sensor of the present invention, comprises a fingertip cushion supporting member having a fingertip cushion supporting surface, and a nail supporting member having a nail supporting surface which is disposed in opposed relationship with the fingertip cushion supporting surface at distance (i.e., interval) smaller than the standard thickness of fingertips. Either of the fingertip cushion supporting member and the nail supporting member are fixed while the other is hinged. The fingertip pulse wave sensor further comprises an elastic body for urging the hinged fingertip cushion supporting member or nail supporting member in the direction in which they are moved toward each other in such a manner that the pressure applied to the hinged fingertip cushion supporting member or nail supporting member becomes constant with respect to variations in the pivot stroke. Notably, these variations in the pivot stroke are caused by the variations in the thickness of the fingertips resting on the fingertip cushion supporting surface. This hinging feature of the present invention enables the adoption of various types of spring structure which are capable of maintaining the pressure applied at a fixed value, unlike a plate spring which directly presses a fingertip.

Present invention allows a fingertip to be gripped between photoelectric elements under a substantially fixed and appropriate pressure which is sufficient to keep the fingertip in place, and yet not to compress a blood vessel to the extent of affecting the measurement accuracy. This enables detection of a stable pulse waveform signal accurately corresponding to changes in the volume of a blood vessel.

In particular, application of the present invention to an acceleration-type pulse wave detector which requires that a stable pulse waveform is detected with a high degree of accuracy, enables highly reliable monitoring of the conditions of peripheral circulation. This feature of the present invention, expectedly will open the way to use of the acceleration-type fingertip pulse wave detectors in clinical applications, including prevention and cure of degenerative diseases caused by circulatory disorders.

DESCRIPTION OF THE PREFERRED EMBODIMENTS

Figure 1:
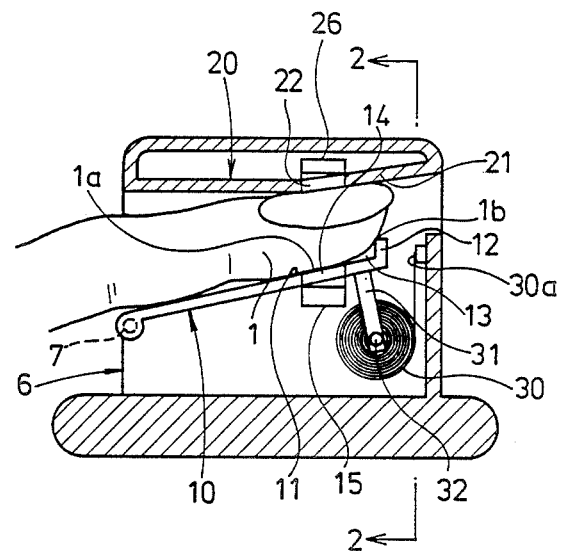
FIG. 1 is a cross-sectional view of the central portion of a fingertip pulse wave sensor, showing a first embodiment of the present invention.
Figure 2:
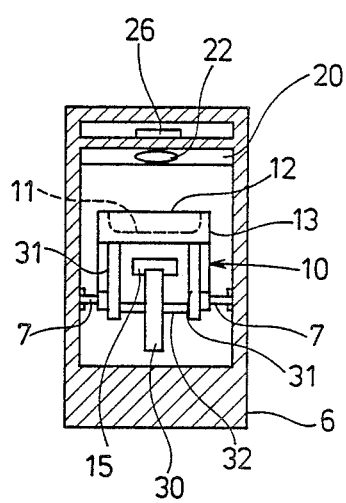
FIG. 2 is a section taken along the line 2—2 of FIG. 1.

FIGS. 1 and 2 show a first embodiment of a fingertip pulse wave sensor according to the present invention.

In this embodiment, the rear end portion of a fingertip cushion supporting plate 10 which acts as a fingertip cushion supporting member, is hinged on shaft rods 7 protruding from the side walls of casing 6. The fingertip cushion supporting plate 10 has at its forward end, a fingertip stopper 12 which is lower than the height of the nail of a fingertip 1 so as not to catch the long nail. The fingertip cushion supporting plate 10 also has guide walls 13 at the two sides thereof which are separated from each other by a distance slightly larger than the standard width of the fingertip 1. A fingertip cushion 1a is placed on the central portion of a fingertip cushion supporting surface 11. The central portion of the fingertip cushion supporting surface is provided with a through-hole 14. A light-emitting element 15 is mounted on the fingertip cushion supporting surface 11 below the through-hole 14.

A nail supporting plate 20 which acts as a nail supporting member, is provided in the upper portion of the casing 6. The nail supporting plate 20 has a nail supporting surface 21 which is inclined at substantially the same angle as that at which the fingertip cushion supporting surface 11 is inclined in a normal state. A hole 22 is formed in the nail supporting plate 20 at a position at which it faces the hole 14. A light-receiving element 26 is mounted on the nail supporting plate 20 behind the hole 22.

A constant-load spiral spring 30 is accommodated in the casing 6 below the fingertip cushion supporting plate 10. The inner end of the spiral spring 30 is pressed onto a rotary shaft 32 rotatably supported by arms 31 handing from the fingertip cushion supporting plate by virtue of its elasticity, and an outer end 30a thereof is fixed to the front surface of the casing 6.

When the measurement is to be conducted, the fingertip 1 is advanced until a forward end 1b thereof abuts against the stopper 12, as shown in FIG. 1. At that time, the fingertip cushion supporting plate 10 is lowered by a distance corresponding to the thickness of the fingertip 1, and the constant-load spiral spring 30 is thereby unwound by a length corresponding to the lowering stroke of the spring 30. Further, the constant load characteristics of the spring enable the pressure generated by the winding force of the spring, to be maintained at an appropriate fixed value. In this way, the fingertip 1 is applied with an appropriate pressure sufficient to keep it in place and yet not to generate distortion in the pulse waveform, which is caused by the excessive pressure applied to the fingertip due to variations in the thickness of the fingertips resting on the fingertip cushion supporting plate. The light emitted from the light-emitting element 15 passes through the hole 14, is transmitted through the fingertip 1, and is received by the light-receiving element 26 which is disposed in opposed relationship with the light-emitting element 15. In the light-receiving element 26, the received light is converted into electrical signals. The thus-generated stable signals accurately representing the changes in the volume of blood in a vein, are supplied to the body (not shown) of a fingertip pulse wave sensor.

Figure 3:
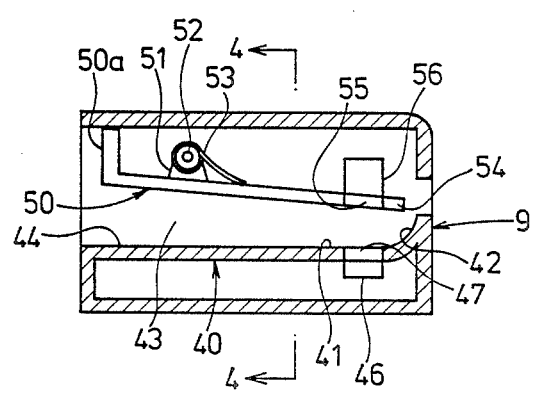
FIG. 3 is a cross-sectional view of the central portion of a fingertip pulse wave sensor, showing a second embodiment of the present invention.
Figure 4:
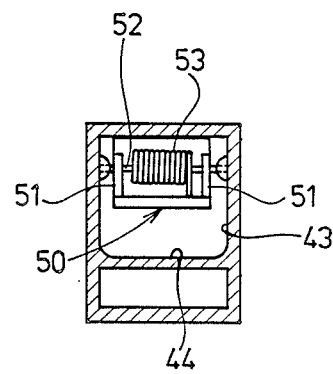
FIG. 4 is a section taken along the line 4—4 of FIG. 3.

FIGS. 3 and 4 show a second embodiment of the present invention. In this embodiment, a fingertip cushion supporting plate 40 is provided in a casing 9. The fingertip cushion supporting plate 40 has a guide surface 44, guide walls 43 and a fingertip stopper 42. The central portion of the fingertip cushion supporting surface 41 is provided with a hole 47. A light-emitting element 46 is disposed on the fingertip cushion supporting surface 41 behind the hole 47.

A nail supporting plate 50 is disposed in the casing 9 substantially parallel to the fingertip cushion supporting plate 40. Bearing portions 51 provided on the two sides of the nail supporting plate 50, are hinged on a pin 52 extending between the side walls of the casing 9. A coil spring 53 is provided on the pin 52. The one end of the coil spring 53 is fixed to the upper surface of the casing 9, and the other end thereof is fixed to the nail supporting plate 50. The coil spring 53 urge the nail supporting plate 50 in the direction in which a curved rear end portion 50a thereof abuts against the upper surface of the casing 9.

The nail supporting plate 50 has a nail supporting surface 54. A hole 55 is formed in the nail supporting plate 50 at a position at which it faces the hole 47. A light-receiving element 56 is mounted on the nail supporting plate 50 behind the hole 55.

When the fingertip 1 is inserted along the guide surface 44 and is then advanced until it abuts against the fingertip stopper 42, the nail supporting plate 50 is raised against the pressure of the coil spring 53 by a distance corresponding to the thickness of the fingertip inserted. At this time, since the rear portion of the nail supporting plate 50 is hinged, the amount of pivot of the coil spring 53 is small with respect to the stroke of the nail supporting plate 54 by virtue of the principles of lever. Further, constant load characteristics are ensured by using a sufficient number of turns (e.g., in the coil spring), and the pressure applied by the spring can be maintained at a constant value with respect to the variations in the thickness of the fingertips.

In any of the above-described embodiments, the fingertip cushion supporting member and the nail supporting member, have a plate-like form. However, the fixed member may also be shaped in a block-like form. Air springs and other types of mechanical springs may be employed as the elastic body which is adapted to maintain the pressure at a constant value with respect to the variations in the pivot stroke which are caused by the differences in individuals. Furthermore, the first embodiment may also employ a coil spring, and the second embodiment may also use a constant-load spiral spring.

What is claimed is:

1. A fingertip pulse wave sensor, comprising:
   a casing;
   fingertip cushion supporting member hinged relative to said casing and having a fingertip cushion supporting surface;
   a nail supporting member fixed relative to said casing and having a nail supporting surface which is disposed in opposed relationship with said fingertip cushion supporting surface at a distance smaller than the standard thickness of fingertips;
   a rotatable shaft coupled to the fingertip cushion supporting member;
   elastic means for urging said hinged fingertip cushion supporting member toward said nail supporting surface in such a manner that the pressure applied by said elastic means becomes substantially constant with respect to the variations in the pivot stroke caused by the variations in the thickness of said fingertips resting on said fingertip cushion supporting member, the elastic means including one of a constant-load spiral spring and coil spring having one end mounted to the rotatable shaft and another end engaging the casing;
   a light-emitting element disposed on either of said fingertip cushion supporting surface and said nail supporting surface; and
   a light-receiving element disposed on the other of said fingertip cushion supporting surface and said nail supporting surface.

2. A fingertip pulse wave sensor, comprising:

a casing;

fingertip cushion supporting member fixed relative to said casing and having a fingertip cushion supporting surface;

a nail supporting member hinged relative to said casing and having a nail supporting surface which is disposed in opposed relationship with said fingertip cushion supporting surface at a distance smaller than the standard thickness of fingertips;

a pivot pin mounted on the nail supporting member;

elastic means for urging said hinged nail supporting member toward said fingertip cushion supporting surface in such a manner that the pressure applied by said elastic means becomes substantially constant with respect to the variations in the pivot stroke caused by the variations in the thickness of said fingertips resting on said fingertip cushion supporting member, the elastic means including one of a constant-load spiral spring and a constant-load coil spring, said one of the spiral spring and coil spring having one end mounted to the pivot pin and another end engaging the nail supporting member;

a light-emitting element disposed on either on said fingertip cushion supporting surface and said nail supporting surface; and a light-receiving element disposed on the other of said fingertip cushion supporting surface and said nail supporting surface.

* * * * *